US012797644B2

(12) United States Patent
Goldberg

(10) Patent No.: US 12,797,644 B2
(45) Date of Patent: Nov. 17, 2026

(54) USE OF ULTRASONIC TONES TO INDUCE PHYSIOLOGICAL EFFECTS

(71) Applicant: REVIVA SOFTWORKS LTD, London (GB)

(72) Inventor: Jules Goldberg, London (GB)

(73) Assignee: Reviva Softworks Ltd., London (GB)

( * ) Notice: Subject to any disclaimer, the term of this patent is extended or adjusted under 35 U.S.C. 154(b) by 0 days.

(21) Appl. No.: 19/158,655

(22) PCT Filed: Feb. 23, 2024

(86) PCT No.: PCT/GB2024/050508
§ 371 (c)(1),
(2) Date: Aug. 21, 2025

(87) PCT Pub. No.: WO2024/175934
PCT Pub. Date: Aug. 29, 2024

(65) Prior Publication Data

US 2026/0115497 A1 Apr. 30, 2026

(30) Foreign Application Priority Data

Feb. 23, 2023 (GB) ...................................... 2302637
Dec. 21, 2023 (GB) ...................................... 2319856

(51) Int. Cl.
*A61N 7/00* (2006.01)

(52) U.S. Cl.
CPC ........ *A61N 7/00* (2013.01); *A61N 2007/0026* (2013.01)

(58) Field of Classification Search
None
See application file for complete search history.

(56) References Cited

U.S. PATENT DOCUMENTS 4,319,349 A * 3/1982 Hackett ................. G01S 15/523 367/136
2020/0367810 A1* 11/2020 Shouldice ............ A61B 5/4818
2023/0022546 A1 1/2023 Malchano et al.

FOREIGN PATENT DOCUMENTS

EP 3515290 B1 6/2023
GB 2609061 A 1/2023
JP H01218463 A 8/1989
JP 2005334163 A * 12/2005
KR 20090013361 A 2/2009
(Continued)

OTHER PUBLICATIONS

KR-20170136742-A—machine translation (Year: 2017).*
JP-2005334163-A—machine translation (Year: 2005).*

*Primary Examiner* — Christopher Koharski
*Assistant Examiner* — Renee C Langhals
(74) *Attorney, Agent, or Firm* — Dierker & Kavanaugh, P.C.

(57) ABSTRACT

Disclosed are techniques of inducing physiological effects using combinations of two or more ultrasonic tones to produce low-frequency fluctuations in acoustic pressure at one or more biologically characteristic frequencies. Combining ultrasonic tones can trigger powerful awareness stimulating effects, and is distinguished from conventional acoustic entrainment techniques such as binaural beats as audible sound frequencies are not employed. Alternative frequency pressure fluctuations trigger other physiological effects such as clearing of respiratory passages.

12 Claims, 9 Drawing Sheets

(56) References Cited

FOREIGN PATENT DOCUMENTS

| | | | | | |
|---|---|---|---|---|---|
| KR | 20170136742 | A | * | 12/2017 | ......... A61N 1/36025 |
| WO | 2019225773 | A1 | | 11/2019 | |
| WO | 2022185025 | A1 | | 9/2022 | |

* cited by examiner

USE OF ULTRASONIC TONES TO INDUCE PHYSIOLOGICAL EFFECTS

FIELD OF THE INVENTION

The present invention relates to inducing physiological effects using combinations of ultrasonic tones, and particularly to combining two or more ultrasonic tones to produce low-frequency fluctuations in acoustic pressure at one or more biologically characteristic frequencies.

TECHNICAL BACKGROUND

There is extensive research that acoustic energy is capable of having stimulant effects on the human body when oscillating at specific frequencies. A large body of research has focused on using audible sound waves with oscillation patterns ranging from 3-40 Hz to promote beneficial states such as concentration, learning, or relaxation via neural entrainment. Sensory stimulation using gamma frequencies, (~25-100 Hz) has emerged as a promising treatment to offset cognitive decline associated with Alzheimer's disease ("Gamma Oscillations in Alzheimer's Disease and Their Potential Therapeutic Role", Traikapi et al, Frontiers in Systems Neuroscience, December 2021). Other studies have found that acoustic vibrations in the range 100-200 Hz resonate with the sinuses and can be helpful for treating nasal congestion.

Ultrasonic tones, generally having a frequency above 16 kHz, are much less perceptible to humans than tones within the audible hearing range. Additionally, ultrasonic tones carry far more energy than audible soundwaves at lower frequencies, with the energy carried by an acoustic wave being proportional to the square of its frequency.

Medical applications of ultrasound typically use frequencies in the MHz range, whilst non-invasive neuromodulation is described in relation to frequencies from 0.5-3 MHz ("A review on ultrasonic neuromodulation of the peripheral nervous system: enhanced or suppressed activities?", Feng et al, Applied Sciences, April 2019). Ultrasonic neuromodulation is typically based on pulsing of a single frequency tone between binary states.

SUMMARY OF INVENTION

The inventor has discovered that it is possible to use ultrasound of longer wavelengths and lower power than employed in medical neuromodulation, to induce physiological effects consistent with a neurological stimulus, such as increased alertness. The longer wavelengths, associated with a frequency range of 16-48 kHz, and lower power infers a fundamentally different mode of action from medical ultrasound. This type of longer wavelength, lower power ultrasound is within the output capabilities of smartphones, whilst being inaudible.

Ultrasonic waves propagate through media such as air via a transference of kinetic energy between neighbouring particles. When oscillating air particles make contact with a higher density object, such as a human body, a portion of energy will be reflected back in the air whilst a portion will be absorbed into the body. The reflected energy can be analysed to detect movements via Doppler analysis and used in other imaging techniques. The absorbed energy, when propagated by low-power smartphone speakers, is not neurologically stimulating if it is constant over time. Consequently, a constant amplitude, low-power ultrasonic tone can be employed to detect body movements and breathing for applications such as sleep tracking, without causing any neurological effects on the user.

The inventor has observed that if the amplitude of an ultrasonic signal is varied over time, by combining multiple frequency tones or with an alternative amplitude modulation pattern, users can experience neurological effects such as increased alertness. This technique produces a constantly fluctuating acoustic pressure, and induces continuous stimulation which is fundamentally different to that achieved by the binary pulsing of a single frequency tone. The neurological effects induced by these methods are substantially more powerful would be induced by a low-frequency, audible tone of equal signal amplitude, and it can thus be inferred that the stimulation effects are caused by energetic variations induced by ultrasonic modulation, rather than by the maximal signal amplitude, or by the overall signal energy, which is not neurologically stimulating when constant.

The inventor puts forward that one mode of stimulation effect occurs via nerve receptors in the skin detecting pressure changes, in a manner analogous to a light, rhythmic touch pattern, which then transmits electrical impulses to the brain triggering effects such as increased alertness at beta and gamma frequencies. When biologically characteristic frequencies are matched, the effects are more consistent with a mechanical stimulation, rather than an auditory stimulation.

Neural entrainment is a phenomenon whereby neural oscillations naturally synchronise with the frequency of an external stimulus, and fluctuations in acoustic pressure using ultrasonic tones induces feelings consistent with this.

Combining ultrasonic tones can trigger powerful awareness stimulating effects, and is also distinguished from other acoustic entrainment techniques such as binaural beats, as audible sound frequencies are not employed and the user does not need to wear headphones. The proposed mode of action, with fluctuating pressure on nerve receptors in the skin triggering electrical impulses to the brain, makes this entrainment technique more analogous to a mechanical or electrical stimulation rather than auditory techniques.

It is not natural for neural oscillations to have a fixed frequency for extended intervals, and so tolerance of the neural stimulation effect is enhanced, in embodiments, by employing a duty cycle, for example 5 seconds of stimulus followed by 25 seconds of rest.

Higher amplitude acoustic pressure fluctuations over 20 dB may be felt as a rhythmic breeze in the air, and cause motion sensations deeper in the body. Higher amplitude acoustic pressure fluctuations may induce physiological effects separate from, and in addition to, the neurological effects described above. For example, high amplitude acoustic pressure fluctuations, within a frequency range of 100-200 Hz, are particularly effective for clearing sinus congestion.

It may be necessary to control the overall variation in pressure and the duration of the stimulus to achieve desired effects, with low amplitude variations in pressure triggering neural stimulation and with higher amplitude variations suitable for congestion clearing and deeper stimulation effects. Overstimulation in terms of either the pressure variation or the duration of exposure can lead to negative outcomes such as headaches, and so it is important to be able to control the level of stimulation with techniques such as duty cycles, time-limited or scheduled interventions, and triggered interventions based on feedback mechanisms such as analysis of the user's breathing.

The inventor's prior patent application GB 2302637.0, filed 23 Feb. 2023 and entitled "Use of Amplitude Modulated Ultrasound for Motion Tracking and Inducing Awareness in a Target", the priority of which is claimed, presents a technique of using ultrasound in motion tracking, based on measurement of Doppler shifts to an ultrasonic pilot tone. By modulating the ultrasonic pilot tone at a rate according to the stimulus frequency, it is possible to induce a stimulus in a target without compromising motion estimation. This can be particularly advantageous where motion tracking is used in a sleep tracking application, where the ultrasonic pilot tone is inaudible, but where a stimulus can be used to improve the quality of sleep.

As such, the inventor has discovered that not only is it possible to produce low-frequency fluctuations in acoustic pressure using ultrasound to induce physiological effects, but it is possible to combine this effect with another application of ultrasound, namely motion-tracking with an ultrasonic tone.

The embodiments described herein employ the same combination of advantages, of ultrasonic stimulus induction and motion-tracking, based on combining two or more ultrasonic tones of different frequencies. One or more beat frequencies of the combination corresponds to a respective one or more stimulus frequencies, while one of the ultrasonic tones also serves as a pilot tone for motion tracking.

More generally, the inventor has appreciated that motion-tracking function is not an essential feature of all of the embodiments described, and that combining ultrasonic tones to induce physiological effects can be employed beneficially in a myriad of applications.

According to an aspect of the present invention, there is provided an apparatus for inducing one or more physiological effects in a target, comprising: a speaker, configured to output two or more ultrasonic tones, wherein the two or more ultrasonic tones combine to produce fluctuations in acoustic pressure at one or more frequencies corresponding to one or more respective biologically characteristic frequencies of the target.

The two or more ultrasonic tones may have frequencies in the range of 16-48 KHz.

The speaker may be configured to activate one or more of the two or more ultrasonic tones according to a duty cycle which is less than 100%, in which output of the one or more ultrasonic tones is stopped periodically.

In embodiments the speaker is configured to transmit a first ultrasonic tone having a first frequency, a second ultrasonic tone having a second frequency higher than the first frequency, and a third ultrasonic tone having a third frequency higher than the second frequency, wherein the amplitude of the second ultrasonic tone is greater than the amplitudes of the first and third ultrasonic tones. In such embodiments, the spacing between the first frequency and the second frequency may be equal to the spacing between the second frequency and the third frequency, the amplitudes of the first and third ultrasonic tones may be equal, and the amplitude of the second ultrasonic tone may be at least double the amplitude of the first ultrasonic tone, such that the combination of the first, second and third ultrasonic tones produces a sinusoidal fluctuation in acoustic pressure at the frequency difference of the first and second ultrasonic tones.

The apparatus may further comprise a controller, and a microphone configured to sample a signal reflected by the target; wherein the controller is configured to estimate motion of the target based on frequency analysis of the sampled signal, and determination of a Doppler shift in one or more of the ultrasonic tones.

The two or more ultrasonic tones may have frequencies which are an integer multiple of a sampling rate of the microphone, divided by $2^n$, for integer $n \geq 2$.

The apparatus may further comprising a display for an application, wherein the controller may be arranged to determine inputs to the application using the estimated motion of the target.

The speaker may be configured to combine the two or more ultrasonic tones with music or soundscapes.

The one or more biologically characteristic frequencies may be in ranges associated with neurological activity.

The one or more biologically characteristic frequencies may include one or more resonant frequencies of respiratory pathways of the target.

According to an aspect of the present invention, there is provided a sleep-tracking apparatus comprising the above apparatus, wherein the speaker is configured to output the two or more ultrasonic tones in dependence on one or more of:

- a predetermined time schedule;
- a rapid eye movement sleep state being detected;
- a deep sleep state being detected;
- a light sleep state being detected;
- body movement;
- breathing sounds and/or presence of snoring; or
- breathing pattern.

According to an aspect of the present invention, there is provided a method of inducing one or more physiological effects in a target, comprising outputting two or more ultrasonic tones, wherein the two or more ultrasonic tones combine to produce fluctuations in acoustic pressure at one or more frequencies corresponding to one or more respective biologically characteristic frequencies of the target.

The method may comprise modulating the two or more ultrasonic tones according to a duty cycle which is less than 100%, in which output of the two or more ultrasonic pure tones is stopped periodically.

According to another aspect of the present invention, there is provided a computer program, which, when executed by an apparatus comprising a controller and a speaker, is arranged to perform the above method.

In embodiments, a combination of three ultrasonic tones, with particular relative weightings and frequency offsets, produces an interference signal having a frequency spectrum which is the same as, or similar to, that of a single ultrasonic tone, modulated at a low-frequency, as set out in GB 2302637.0. Further, motion-tracking can be performed based on observing Doppler shifts from the ultrasonic tone frequencies.

More generally, more than one stimulus frequency can be achieved by using different frequency spacings between pairs of ultrasonic tones. The nature and intensity of the stimulus can be controlled by varying the relative weightings of the ultrasonic tones, which affects the fluctuations in acoustic pressure of the combined signal, and by switching one or more of the ultrasonic tones on and off according to a duty cycle appropriate for a particular application, so as to regulate exposure of the target to pressure fluctuations, and to enable sufficient recovery time.

The ultrasonic tones which are used can be generated by readily-available devices such as smartphones.

BRIEF DESCRIPTION OF DRAWINGS

Embodiments of the present invention will be described by way of example only, with reference to the accompanying drawings, of which.

DETAILED DESCRIPTION

When two sinusoidal signals of different frequencies are combined, the resulting signal has a frequency component at a 'beat' frequency which is the difference between the frequencies of the respective signals. Embodiments of the present invention are based on the principle of combining high frequency ultrasonic signals to cause powerful fluctuations in acoustic pressure at the beat frequency. The beat frequency is selected such that the fluctuations in acoustic pressure induce a physiological effect in the target, which occurs when the beat frequency is close to a biologically resonant frequency of the target. The pressure differential, relative to air pressure, which is caused by the fluctuations, can be shown to be a product of $2\pi f \times \rho \times A$, and as such, is proportional to frequency f, where ρ is the density of air, and A is the signal amplitude.

Whilst any beat interval can be employed to induce acoustic pressure changes and physiological effects, certain precise frequencies also provide compatibility with the Doppler motion tracking system used in embodiments of the present invention, and described in more detail below, enabling integration of stimulation effects into multifaceted applications such as sleep tracking. Such compatibility is achieved by using frequencies which correspond to discrete bin frequencies in an FFT used for the Doppler motion tracking system. Such precise frequencies will all have a property whereby they complete an integer number of phase loops within a number of frames equal to the FFT size. Such frequencies are calculated as an integer multiple of the audio sampling rate, divided by the FFT size (such as 2048). In embodiments, frequencies that are integer multiples of 23.4375 Hz are advantageous, which is an audio sampling rate of 48,000 Hz divided by 2048. This will produce beat frequencies that are also integer multiples of 23.4375 Hz and this is selected for demonstration purposes over rounded frequencies such as 25 Hz. 23.4375 Hz falls within the range of neural oscillations referred to as beta waves (12-30 Hz), generally associated with alertness, concentration and thinking. For brevity, this precise frequency will be henceforth referred to as ~23 Hz.

Figure 1A:
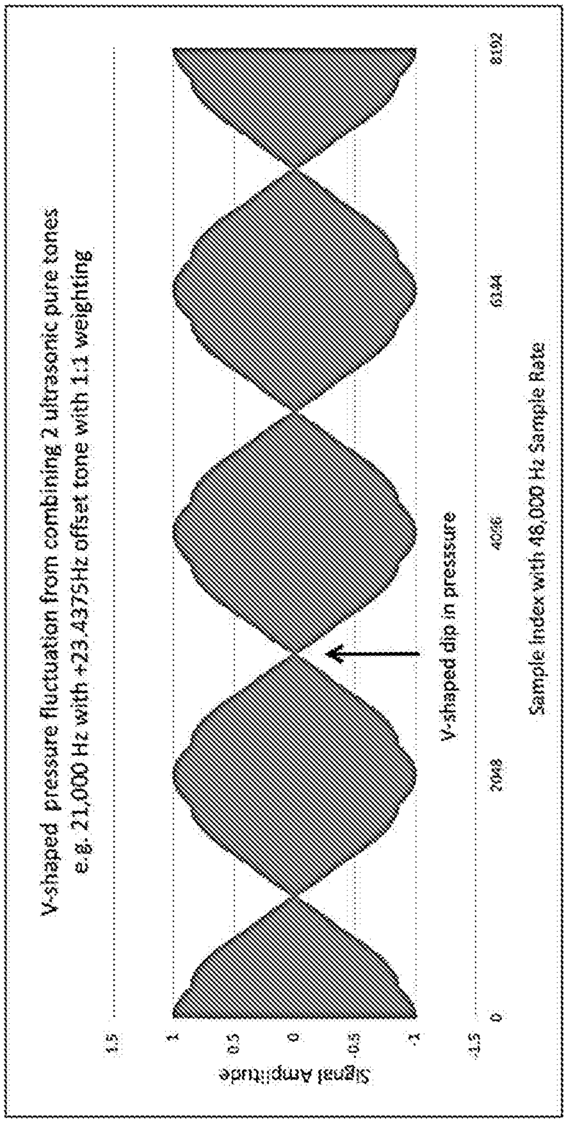
FIG. 1 illustrates an example of a signal which is obtained by combining two ultrasonic tones in embodiments of the present invention.
Figure 1B:
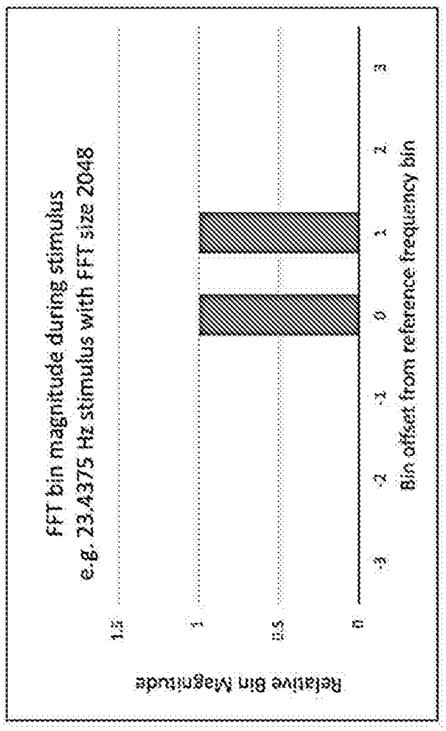

FIG. 1(*a*) illustrates an example of a signal amplitude which is obtained by combining two ultrasonic tones, produced by a speaker of a device such as a smartphone, in an embodiment of the present invention. The first ultrasonic tone has a frequency, referred to herein as a 'reference' frequency, of 21,000 Hz (which is 896×23.4375), while the second ultrasonic tone has a frequency offset from the reference frequency by ~23 Hz. The first and second ultrasonic tones have an equal amplitude weighting.

The combined signal exhibits approximately V-shaped drops in amplitude, with periodic peaks and troughs at a rate of ~23 Hz—this rate is the beat frequency which is the offset between the two ultrasonic tones. When the two ultrasonic tones are output by the speaker in the vicinity of a target, the target experiences fluctuations in acoustic pressure at a frequency of ~23 Hz. The fluctuations in acoustic pressure induce a stimulation effect in the target.

FIG. 1(*b*) illustrates the frequency spectrum, obtained using an FFT of size 2048, of the combined signal, showing two speaks in adjacent frequency bins spaced by ~23 Hz. Frequency bin with index zero is the bin which corresponds to the reference frequency.

In other embodiments, more than two ultrasonic tones are combined. In some embodiments, a 'triad' of three equally spaced ultrasonic tones, in which the intermediate reference-frequency ultrasonic tone has at least double the amplitude weight of the higher and lower peripheral ultrasonic tones, has particular advantages. A signal obtained by the combination of three such ultrasonic tones is shown in FIG. 2(*a*).

Figure 2A:
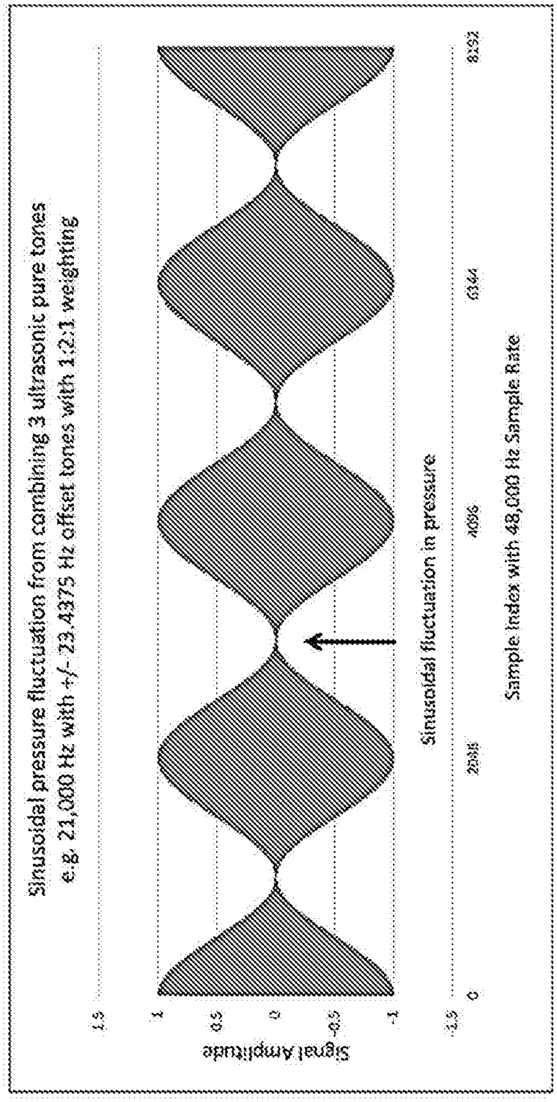
FIG. 2 illustrates an example of a signal which is obtained by combining three ultrasonic tones in embodiments of the present invention.
Figure 2B:
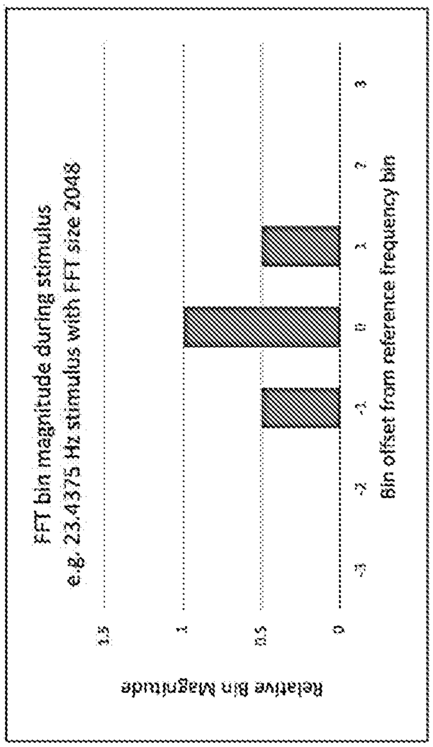

In contrast to FIG. 1(*a*), the combined signal of FIG. 2(*a*) shows sinusoidal fluctuations in acoustic pressure, rather than the V-shaped fluctuations associated with a combination of two ultrasonic tones. The combined signal is equivalent to a single ultrasonic tone of 21,000 Hz which is amplitude-modulated with a Hann function of length 2048 frames. The sinusoidal fluctuations represent a smoother variation in acoustic pressure, with a less abrupt change between decreasing and increasing acoustic pressure, compared to the V-shape of FIG. 1(*a*), with a greater overall variation in acoustic pressure and stimulation effect. The smoother transition at the lower end of the acoustic pressure fluctuation is a softer, more pleasant experience for a target, regardless of the stimulus frequency used. Furthermore, the FFT representation of the tones produces a symmetrical layout around the reference frequency, with an equal magnitude offset tone on either side of the reference frequency. This balanced, symmetrical layout has advantages when applied to a motion tracking system, which aims to identify Doppler shifts relative to a reference frequency.

The frequency spectrum of the combined signal is shown in FIG. 2(*b*), based on a FFT of size 2048. Here, the three peaks in adjacent bins of indices −1, 0 and 1, relative to the reference frequency, are shown, in which the central peak is double the height of the two outer peaks.

In the case of combining three ultrasonic tones of different frequencies, it is possible to use a different frequency offset between the lowest frequency ultrasonic tone and the reference frequency ultrasonic tone, from that used between the reference frequency ultrasonic tone and the highest frequency ultrasonic tone. As a result of this, it is possible to generate two different beat frequencies which can induce multiple physiological effects simultaneously. For example, it is possible to configure an embodiment in which beta stimulation and sinus-clearing effects are provided simultaneously. In embodiments, this is achieved using offsets of ~140 Hz and ~117 Hz, which also introduces a beat frequency at the offset difference of ~23 Hz.

The use of three or more ultrasonic tones opens up the extent to which the system can be configured for a particular application. As well as the possibility of using an asymmetric or irregular arrangement of frequency offsets, it is possible to use more combinations of amplitude weightings, which can improve the experience of receiving a particular stimulus.

The combination of ultrasonic tones may be controlled in a way in which the amplitudes of each ultrasonic tone and the duty cycle of their delivery are configured for a particular application. Further, by adapting the relative weighting of the ultrasonic tones, the variations in acoustic pressure can be influenced accordingly.

Figure 3A:
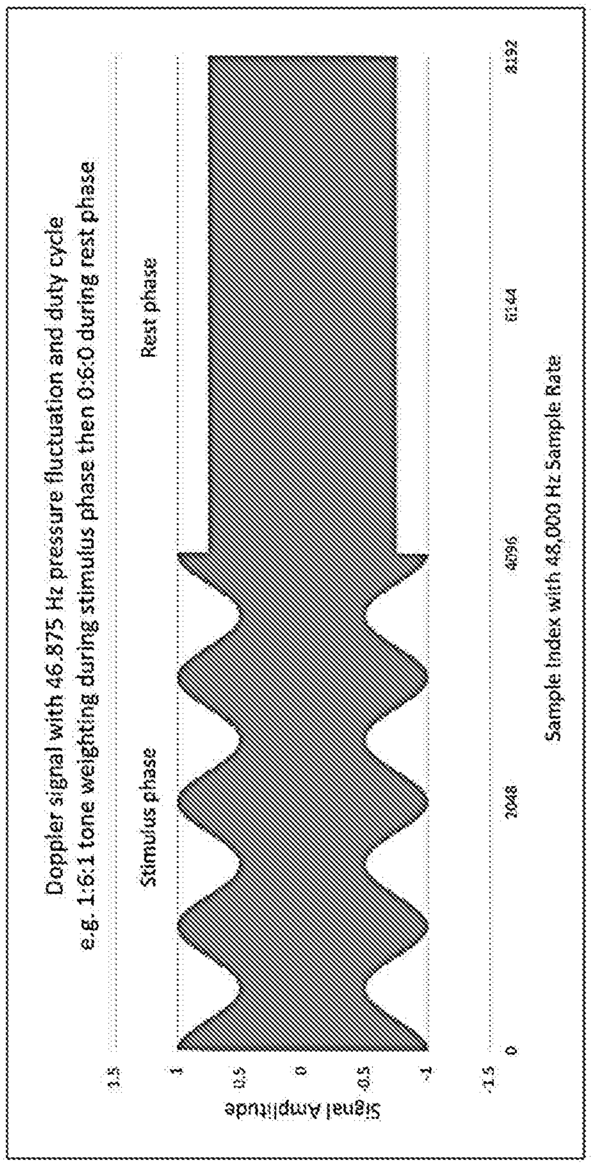
FIG. 3 illustrates an example of a signal which is obtained by combining three ultrasonic tones, and applying a duty cycle, in further embodiments of the present invention.
Figure 3B:
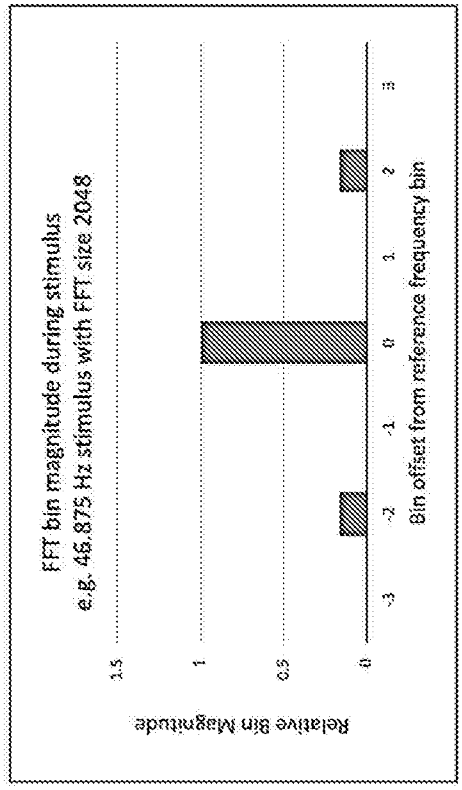

For example, FIG. 3(*a*) shows the signal which is obtained by combining three ultrasonic tones spaced by 46.875 Hz, with a relative weighting of 1:6:1 when the ultrasonic tones are expressed in order of frequency. The stimulus phase is followed by a rest phase of the same length as the stimulus phase, i.e. the duty cycle of the stimulus phase is 50%. In the rest of phase of FIG. 3(*a*), the three signals are weighted in the ratio 0:6:0. The offset frequency signals are zeroed to remove the stimulus effect, whilst the reference frequency is preserved to maintain motion-tracking capabilities, in a manner described below. If motion-tracking is not required, the reference frequency may also be zeroed in the rest phase.

The FFT of the stimulus phase is shown in FIG. 3(*b*), again using size 2048. The frequency spacing of 46.875 Hz means that frequency peaks are seen in bins with indices −2, 0 and +2, relative to the reference tone, and the 1:6:1 amplitude weighting is shown.

The increased weighting of the reference frequency ultrasonic tone is beneficial when combined with motion tracking, as it enables a weaker stimulation effect when combined with a more powerful reference tone for motion tracking. The stimulation effect is relative to a higher baseline acoustic pressure arising from the reference tone, in contrast to the arrangements of FIGS. 1(*a*) and 2(*a*) where the minimum amplitude is periodically zero.

In a further embodiment, ultrasonic tones are combined to create an acoustic pressure fluctuation in the approximate range 100-300 Hz that resonates in one or more respiratory pathways of the target. These frequencies are associated with human humming and meditative chanting which have been demonstrated to reduce nasal congestion and enhance gas exchange whilst breathing. In stimulating respiratory pathways in this way with fluctuations in acoustic pressure, it is possible to stimulate movement of material in a way which assists with breathing by clearing, for example, nasal passages.

In another embodiment, ultrasonic tones are combined to produce an acoustic pressure fluctuation at 140.625 Hz as part of a two-minute nasal congestion clearing application. To assist the user's awareness that the congestion clearing effect is acoustically generated, an audible tone may be played at the same frequency of the fluctuation. Furthermore, by selecting a precise frequency compatible with the Doppler motion system described below, motion responsive interactive visualisations can be displayed to encourage the user's breathing practice. The user's breathing rate can also be estimated and displayed dynamically in real time via analysis of the reflected ultrasonic tones.

Figure 4:
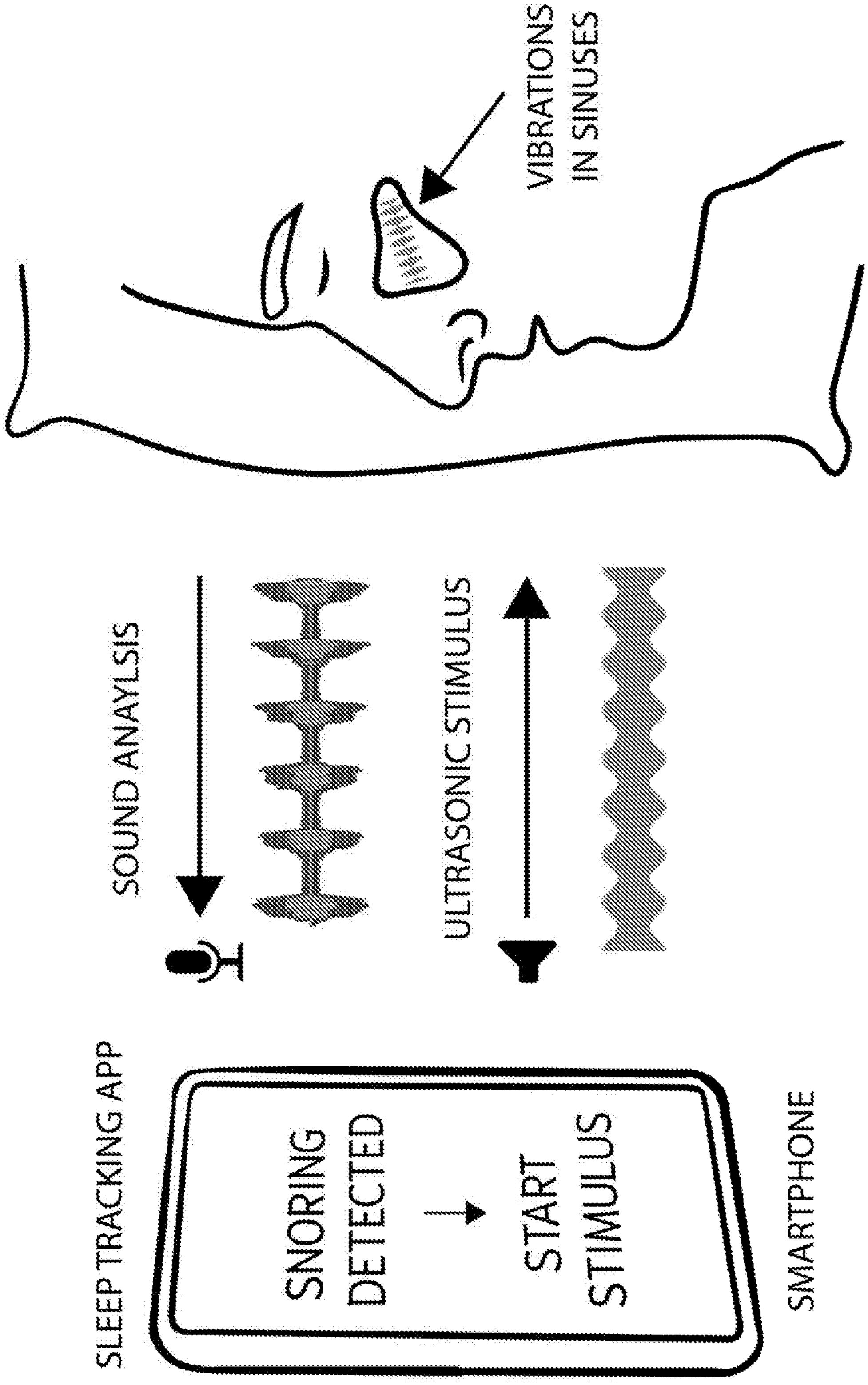
FIG. 4 illustrates an example of the operation of an application to improve breathing, according to embodiments of the present invention.

Clearing of respiratory passages can be used advantageously when a target is sleeping, in order to improve their breathing, reduce snoring, and reduce sleep apnoea. In an embodiment shown in FIG. 4, a device such as a smartphone detects that a target is snoring based on audio captured by a microphone of the smartphone. On detecting snoring, a stimulus phase is started or controlled, targeting respiratory passages. The microphone detects whether snoring is reduced, and if it is, stimulation is either reduced or stopped altogether. In alternative embodiments, the audio is captured by an external device and provided to the smartphone. In alternative embodiments, breathing disturbances are detected by an external device such as a wrist or mattress-based motion-tracking system, and are indicated to the smartphone.

Employing these sleep enhancement techniques using tone frequencies optimised for Doppler measurement enables the user's body movements and breathing to be simultaneously measured enabling a detailed analysis of the user's sleep. The stimulus effect can be controlled without interruption of these sleep tracking capabilities by employing a primary reference tone that is maintained throughout the night for its motion tracking capabilities, and then controlling stimulation effects via the control of weaker secondary tones at frequencies offset from the reference frequency to create acoustic pressure fluctuations via interference with the primary tone.

Figure 5:
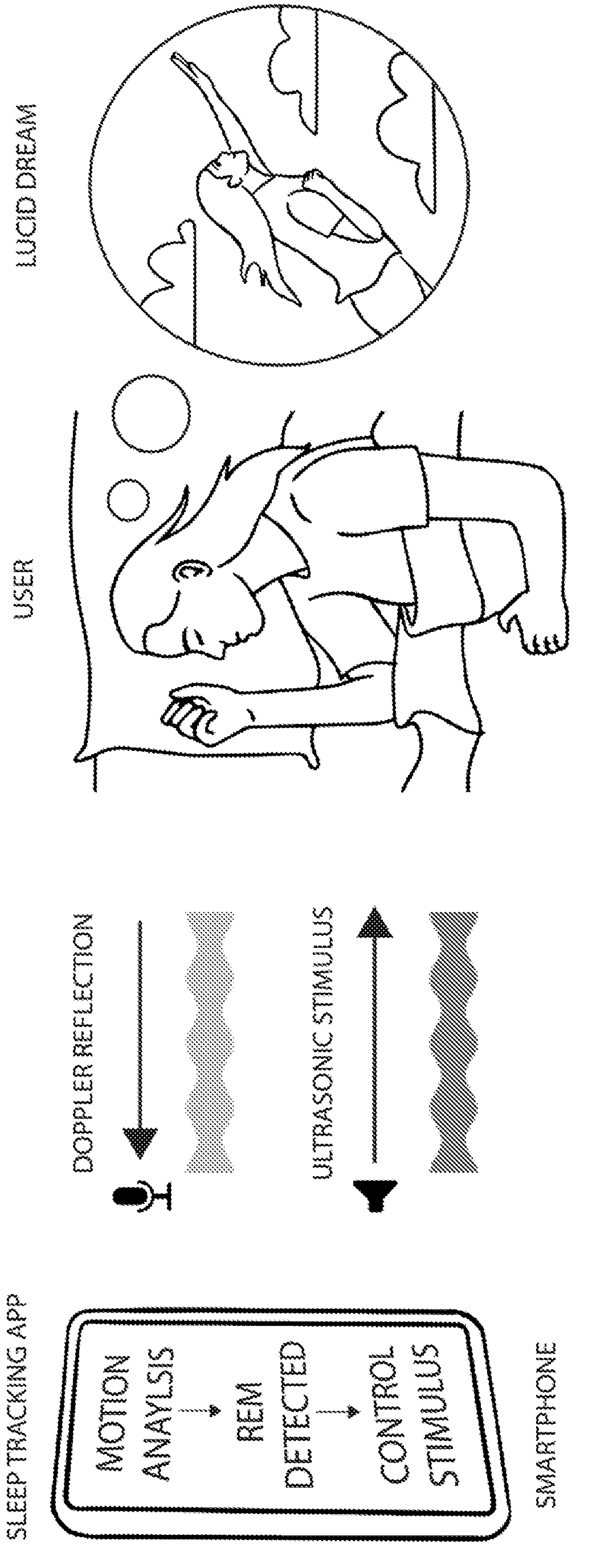
FIG. 5 illustrates an example of the operation of an application to encourage lucid dreaming, according to embodiments of the present invention.

In another embodiment, illustrated in FIG. 5, information derived from reflection of the primary motion tone can be used to infer the user's sleep state. For example, during REM sleep breathing tends to be faster and more irregular compared to deep sleep. Upon estimation that the user has entered a REM sleep stage, indicating that the user is dreaming, an acoustic pressure stimulation in the beta or gamma range is employed by controlling ultrasonic tones at frequencies offset from the reference frequency, with the aim of enhancing dreaming lucidity. Similarly to the neural entrainment application presented above, the lucid dreaming stimulus features a duty cycle to allow the mind to roam freely in between short bursts of stimulation. The stimulus duty cycle may also be combined with a quiet soundscape to influence the lucid dream. Lucid dreaming can provide insights into the user's unconscious mind and can be a powerful therapeutic aid. In alternative embodiments, the user's sleep state is inferred from audio information, or information from a system external to the apparatus of the embodiments, instead of, or in addition to, the information derived from reflection of the primary tone.

Biologically characteristic frequencies may vary from target to target, and may be derived in advance, using, for example, one or more imaging techniques to measure sinus dimensions. Alternatively, the frequencies may be identified empirically by adjusting the beat frequency of the ultrasonic tones and observing resonant effects in the body such as tingling sensations in the sinuses.

Motion Estimation

Figure 8:
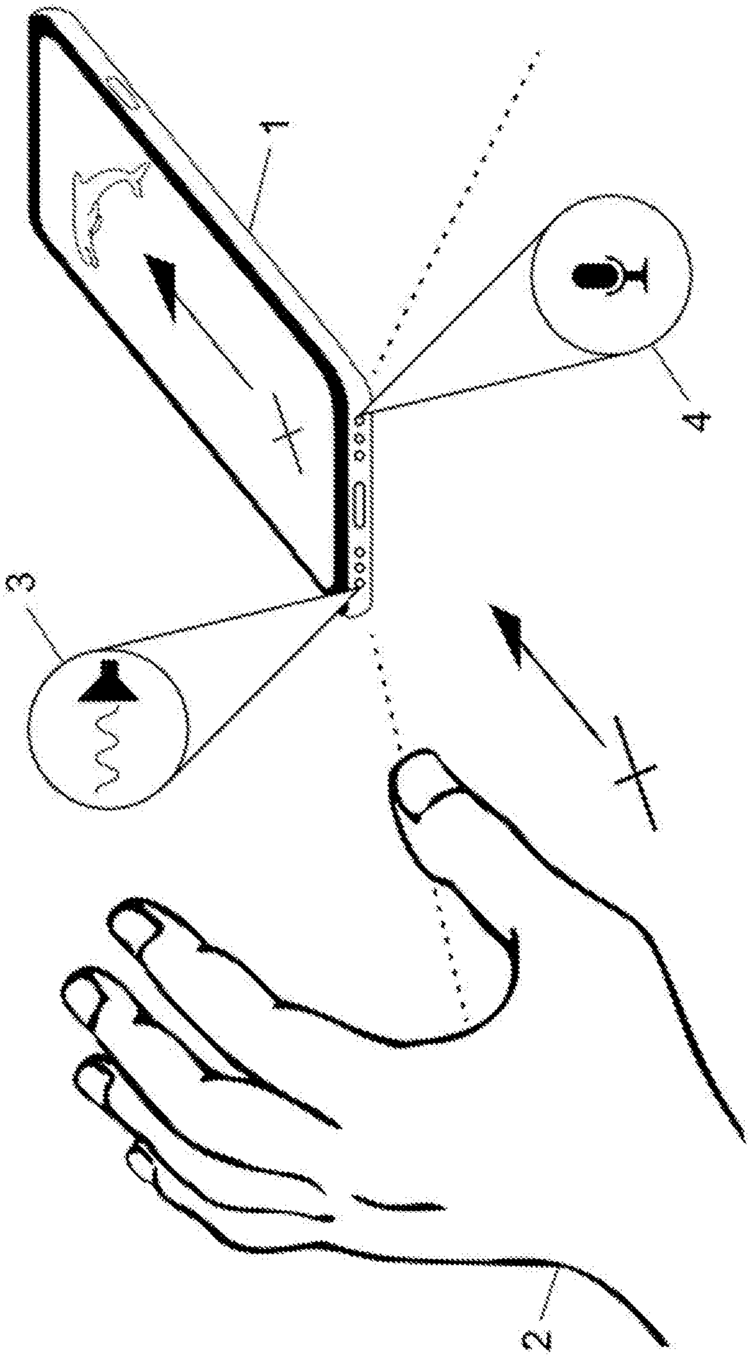
FIG. 8 illustrates the principle of motion tracking of embodiments of the present invention.

In each of the embodiments described above, it is possible to use one or more of the ultrasonic tones as pilot tones for a Doppler motion-tracking system. FIG. 8 illustrates the principle of motion tracking of embodiments of the present invention, in the context of a device 1 which may be used for tracking motion of a target 2, comprising a speaker 3 and a microphone 4. In the illustrated configuration, the device is a smartphone, and the target 2 is a user moving in the vicinity of the smartphone. The device comprises processing means (not shown) configured to control the speaker 3 and the microphone.

In embodiments of the present invention, motion is tracked based on analysis of reflection of one or more ultrasonic tones from the target. If the target is moving, the frequency of the signal reflected directly back to the microphone is Doppler-shifted, as known in the art. If the target moves towards the microphone, the frequency of the reflected signal increases. If the target moves away from the microphone, the frequency of the reflected signal decreases. Generally, the change in frequency, Δf, relates to the relative velocity Δv between the target and the microphone, in the direction towards the microphone, according to $\Delta f = f_0 \cdot \Delta v / c$, where $f_0$ is the frequency of the transmitted ultrasonic tone, and c is the speed of sound in air. As such, motion of the target can be estimated based on determination of the frequency shift of the received signal.

The frequency shift, Δf, can be estimated in a number of ways, based on spectral analysis of the received signal, and the present invention is not limited to any specific motion estimation technique. Spectral analysis is performed using a Discrete Fourier Transform (DFT) or a Fast Fourier Transform (FFT).

In embodiments, a smart alarm feature is implemented in which detection of the user's body movements triggers the start of a gamma frequency stimulus to wake up the user. The stimulus may begin as soon as motion is detected, or after a predetermined delay, and the stimulus may be introduced gradually so as to wake the user gently. The stimulus may be silent or combined with other sounds such as music or natural soundscapes such as ocean waves.

Figure 6:
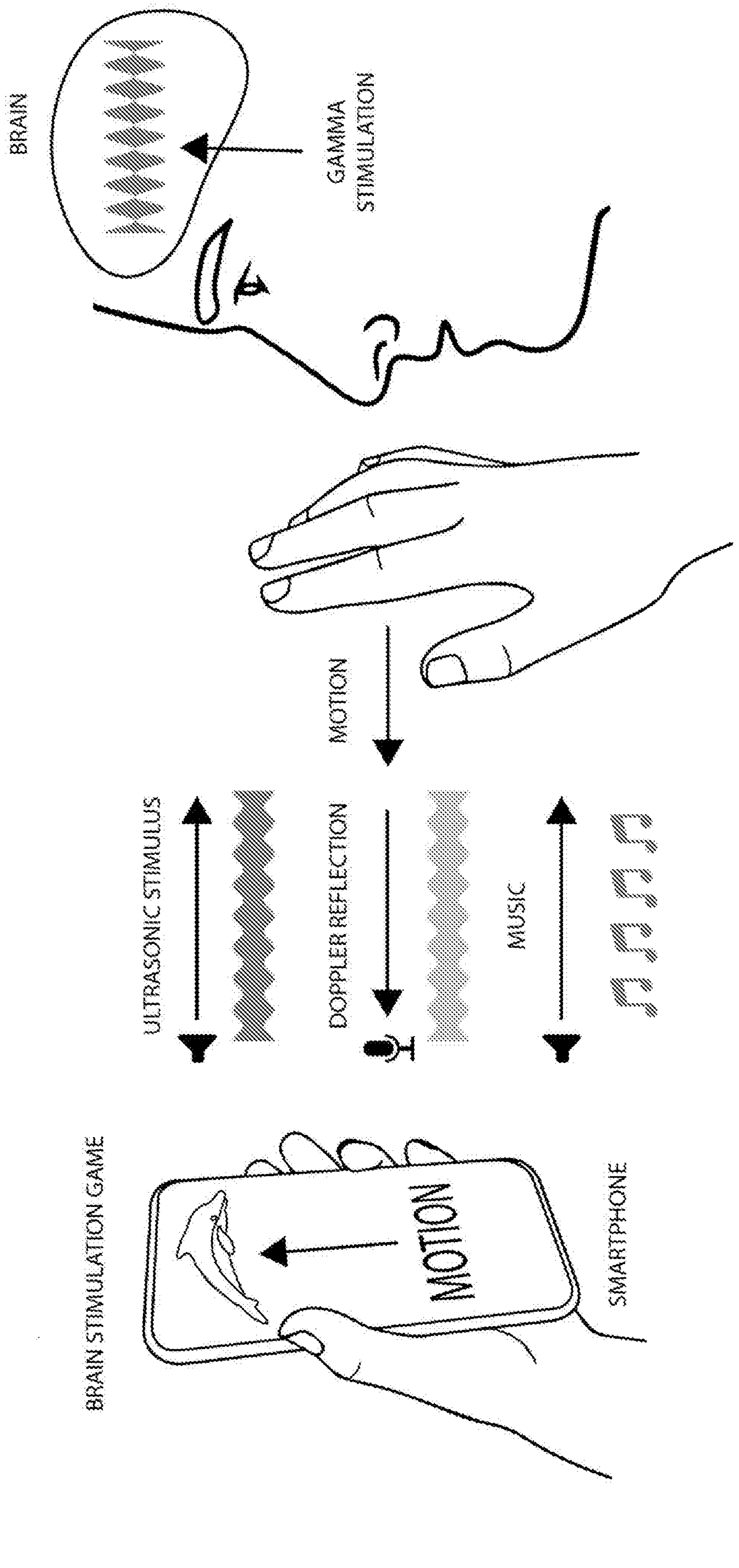
FIG. 6 illustrates an example of the operation of a physical or mental wellness application according to embodiments of the present invention.

In other embodiments, illustrated in FIG. 6, motion estimation is used as the basis of a contactless input to a user interface of an application hosted by a device, such as the smartphone from which the ultrasonic tones are output. A user interacts with the application via a series of gestures involving movement towards and/or away from the microphone, and the gestures are detected and interpreted as particular input commands for the application to process.

While using such an application, a neurological stimulus can be provided simultaneously to the user, without the need for any modification to the pilot tone used for motion estimation. Such embodiments are appropriate in physical and mental wellness applications. For example, mental stimulation may be achieved by targeting beta or gamma (12-100 Hz) frequencies, while the pilot tone is used to track physical gestures of a user in controlling, for example, a puzzle or game application. In doing so, the user is stimulated via neurological entrainment, engagement with the application, and physical movement, improving concentration, awareness and coordination. Such a multifaceted application is particularly effective to aid patients with neurological conditions such as dementia. The ultrasonic stimulus can be combined with music to further increase mental stimulation.

In the rest phases of such systems, the pilot tone used for motion tracking can be preserved, with the stimulus stopped by stopping only output of the offset ultrasonic tones, thus creating a constant acoustic pressure which is non-stimulating. In this manner, there is no interruption to the user's ability to interact with the application.

Figure 7:
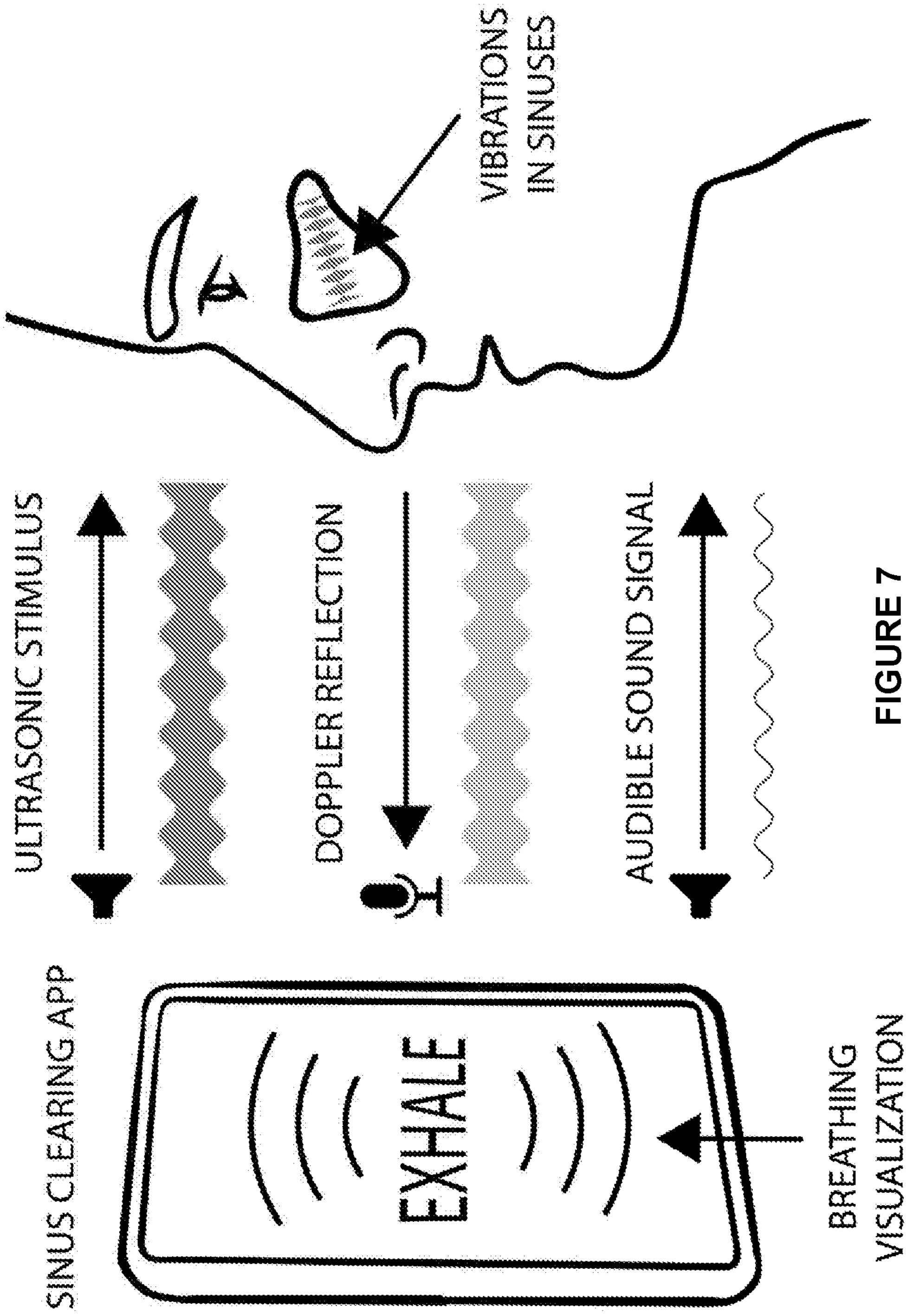
FIG. 7 illustrates an example of the operation of a breathing exercise application according to embodiments of the present invention.

In other embodiments, illustrated in FIG. 7, a display of visualisations, to encourage the user's breathing practice, motion detection, and provision of a stimulus to clear sinuses may be combined, together with the provision of an audible signal to indicate the presence of the stimulus, as described above.

Selection of Pilot Tone Frequency

In some embodiments, it is possible to derive superior motion estimation results by using the technique described in the inventor's prior patent application GB 2319856.7, entitled "Pilot Signal Suppression for Acoustic Doppler Motion Tracking", filed 21 Dec. 2023, priority of which is claimed. In this technique, motion is determined by observing effects caused by Doppler shifts by comparing successive phase-aligned sampling windows and obtaining an FFT or DFT of the comparison. This approach enables suppression of the energy of the pilot tone, relative to the Doppler components.

It is advantageous, particularly in such embodiments of the present invention, for each of the ultrasonic tones which are output to have a frequency which is an integer multiple of a sampling rate of the microphone, divided by $2^n$, for integer $n \geq 2$. In doing so, when samples of the reflected signal are combined in the manner described above, a sampling window containing $2^n$ frames will always contain an integer number of complete phase cycles of each of the ultrasonic tones, enabling comparison with the preceding $2^n$ frames to identify differences caused by Doppler shifted energy components.

Apparatus

Figure 9:
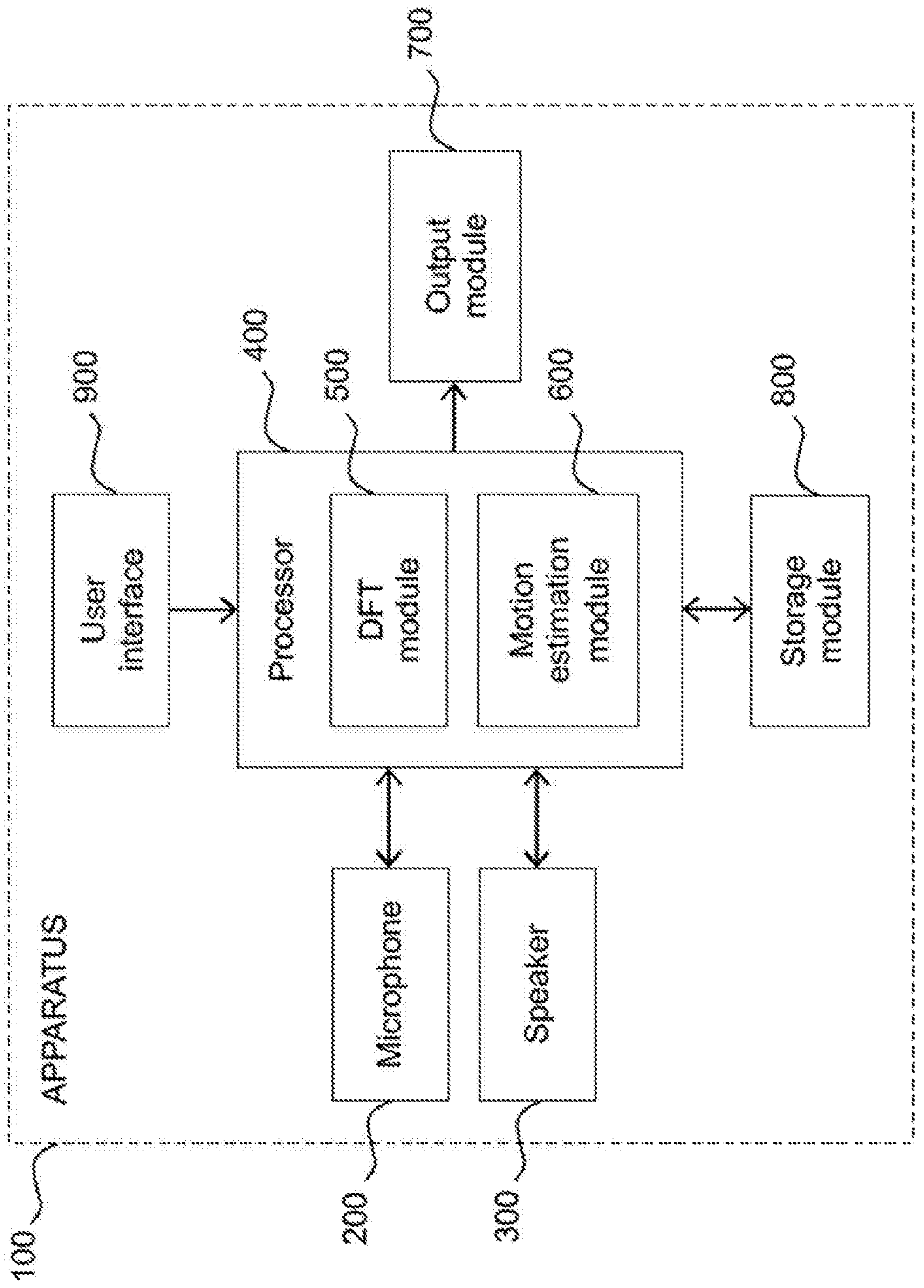
FIG. 9 illustrates an apparatus according to embodiments of the present invention.

FIG. 9 illustrates apparatus 100 for inducing one or more physiological effects in a target, according to embodiments of the present invention. The components illustrated in FIG. 9 represent a standalone apparatus 100 in some embodiments, in which each component is specifically configured to implement a particular function. In other embodiments, the components are part of a device such as a smartphone or tablet. For example, processor 400 may represent a section of computer-readable instructions or code to be downloaded, installed and executed by a processor or controller of a device.

The embodiment of FIG. 9 also comprises components for performing motion estimation, namely the DFT module 500 and the motion estimation module 600, although as described above, such features are not considered essential. The DFT module 500 and motion estimation module 600 may represent execution of further computer-readable instructions. The output module 700 may correspond to display, audio output or communication signal output components of the device, while the microphone 200 and speaker 300 may be those already on-board the device. In yet further embodiments, the microphone and speaker may be off-the-shelf components coupled to a personal computer. Additionally, the apparatus comprises a storage module 800 or memory for storing motion estimation results, and may, in some embodiments, store the computer-readable instructions described above. A user interface module 900 is provided to enable interaction with the apparatus by a user, and may implement a GUI or button-based interface for provision of controls or input of configuration settings.

Although the DFT module 500 and motion estimation module 600 are shown as separate components in FIG. 9 they may, in alternative embodiments, be considered as a single component represented as part of processor 400. In yet further embodiments, such a single component may be separate from, or contained within a central processing unit of the apparatus 100 embodying FIG. 9.

The specific configuration to be used will depend on the application for the motion estimation technique, and examples of such applications are described below. It will also be appreciated that the components of FIG. 9 may be embodied in hardware, software, or a combination of both.

According to the apparatus shown in FIG. 9, the speaker 200 outputs two or more ultrasonic tones. The speaker 200 may also output music or soundscapes. The microphone 300 is employed in order to perform either motion estimation by sampling a reflections of the ultrasonic tones which are output, and/or to detect audio of breathing, depending on the particular application being used.

Motion analysis is performed by the DFT module 500 generating a DFT of signals received by the microphone 200 so as to identify particular spikes in the spectrum representing noise having specific frequency components. Motion estimation module 600 derives an estimate of motion from the position of the spikes in the spectrum relative to the frequency of the pilot tone.

The nature of the output provided by output module 700 is dependent on the specific context in which the embodiment operates, and in some embodiments, the output module 700 is not required at all. In some embodiments, the output module 700 represents a display unit which illustrates detected motion visually so that a user can take particular action. In other embodiments, the output module 700 produces represents an alarm or notification, whether sound and/or light, or some other notification such as an email or message, or operating system notification.

Certain aspects of the apparatus disclosed herein are expressed in the following clauses. The present disclosure is not intended to be limited to such clauses, unless expressly recited in the claims.

Clause 1. An apparatus, comprising: a speaker; a controller for controlling the speaker to output a composite signal; and a microphone configured to sample the composite signal reflected by a user; wherein the controller is configured to estimate motion of the user based on a determination of a shift in the spectral energy distribution of the sampled reflected composite signal, relative to an ultrasonic reference frequency; wherein the composite signal comprises two or more tones having respective ultrasonic frequencies, in which one of the tones of the composite signal has the reference frequency, and the tone frequency separation of each of the two or more tones is a stimulus frequency, such that the composite signal produces fluctuations in acoustic pressure at the stimulus frequency, wherein the controller is arranged to determine a sleep state of the user, and to control the speaker to output the composite signal in dependence on the determined sleep state of the user, wherein the controller is arranged to determine the sleep state of the user based on one or more of: a rapid eye movement sleep state, a deep sleep state, a light sleep state, body movement, or a breathing pattern being determined from the estimated motion.

Clause 2. The apparatus according to clause 1, wherein the two or more ultrasonic tones have frequencies in the range of 16-48 KHz.

Clause 3. The apparatus according to clause 1 or clause 2, wherein the controller is configured to control the speaker to output the composite signal according to a duty cycle in which stimulation is periodically reduced or removed.

Clause 4. An apparatus according to any one of the preceding clauses, wherein the two or more ultrasonic tones have frequencies which correspond to central bin frequencies of a Fast Fourier Transform, FFT, calculated as an integer multiple of a sampling rate of the microphone, divided by $2^n$, for integer $n \geq 2$.

Clause 5. The apparatus according to any one of the preceding clauses, wherein the controller is configured to control the speaker to combine the composite signal with music or soundscapes.

Clause 6. The apparatus according to any one of the preceding clauses, wherein the stimulus frequency is in a range associated with neurological activity.

Clause 7. The apparatus according to clause 6, wherein the neurological activity corresponds to lucid dreaming.

Clause 8. The apparatus according to any one of clauses 1 to 5, wherein the stimulus frequency is a resonant frequency of a respiratory pathway of the user.

Clause 9. The apparatus according to any one of clauses 1 to 5, wherein the stimulus frequency is in a frequency range for stimulation of one or more touch receptors in the user's skin.

It will be appreciated that a variety of implementations will fall within the scope of the claims, the specific implementation depending on at least the desired nature of the physiological effect to be induced and any motion estimation functions to be added. Compatible functions of the embodiments described above may be combined as required in order to form new embodiments, as desired for a particular application.

The invention claimed is:

1. An apparatus, comprising:

a speaker;

a controller for controlling the speaker to output a composite signal; and a microphone configured to receive the composite signal reflected by a user;

wherein the controller is configured to sample the composite signal received by the microphone and is configured to estimate motion of the user based on a determination of a shift in a spectral energy distribution of the sampled reflected composite signal, relative to an ultrasonic reference frequency, wherein the composite signal comprises:

a pilot tone of the ultrasonic reference frequency; and two auxiliary tones of equal amplitude;

wherein a first auxiliary tone of the two auxiliary tones has a first ultrasonic frequency that is offset below the ultrasonic reference frequency, the offset corresponding to a stimulus frequency, a second auxiliary tone of the two auxiliary tones has a second ultrasonic frequency that is offset above the ultrasonic reference frequency by the stimulus frequency, and each of the first and second auxiliary tones has an amplitude that is less than or equal to half the amplitude of the pilot tone, such that an envelope of the composite signal is a sinusoid at the stimulus frequency, and has a symmetrical spectral energy distribution about the ultrasonic reference frequency;

wherein the pilot tone and the two auxiliary tones combine to produce sinusoidal fluctuations in acoustic pressure at the stimulus frequency; and wherein the pilot tone and the two auxiliary tones have frequencies in a range of 16 kHz to 48 KHz.

2. The apparatus according to claim 1, wherein the controller is configured to control the speaker to output the two auxiliary tones according to a duty cycle in which stimulation is periodically reduced or removed.

3. The apparatus according to claim 1, wherein the pilot tone and the two auxiliary tones have frequencies which correspond to central bin frequencies of a Fast Fourier Transform, FFT, calculated as an integer multiple of a rate of sampling the composite signal, divided by $2^n$, for integer $n \geq 2$.

4. The apparatus according to claim 1, further comprising a display for an application, wherein the controller is arranged to determine inputs to the application using the estimated motion of the user.

5. The apparatus according to claim 1, wherein the controller is configured to control the speaker to combine the pilot and the two auxiliary tones with music or soundscapes.

6. The apparatus according to claim 1, wherein the stimulus frequency is in a range associated with neurological activity.

7. The apparatus according to claim 1, wherein the stimulus frequency is a resonant frequency of a respiratory pathway of the user.

8. The apparatus according to claim 1, wherein the stimulus frequency is in a frequency range for stimulation of one or more touch receptors in the skin.

9. A sleep-tracking apparatus, comprising:
a speaker;
a controller for controlling the speaker to output a composite signal; and
a microphone configured to receive the composite signal reflected by a user;
wherein the controller is configured to sample the composite signal received by the microphone and is configured to estimate motion of the user based on a determination of a shift in a spectral energy distribution of the sampled reflected composite signal, relative to an ultrasonic reference frequency,
wherein the composite signal comprises:
a pilot tone of the ultrasonic reference frequency; and two auxiliary tones of equal amplitude;
wherein a first auxiliary tone of the two auxiliary tones has a first ultrasonic frequency that is offset below the ultrasonic reference frequency, the offset corresponding to a stimulus frequency, a second auxiliary tone of the two auxiliary tones has a second ultrasonic frequency that is offset above the ultrasonic reference frequency by the stimulus frequency, and each of the first and second auxiliary tones has an amplitude that is less than or equal to half the amplitude of the pilot tone, such that an envelope of the composite signal is a sinusoid at the stimulus frequency, and has a symmetrical spectral energy distribution about the ultrasonic reference frequency:
wherein the pilot tone and the two auxiliary tones combine to produce sinusoidal fluctuations in acoustic pressure at the stimulus frequency;
wherein the pilot tone and the auxiliary tones have frequencies in a range of 16 kHz to 48 KHz; and
wherein the controller is configured to control the speaker to output the two auxiliary tones in dependence on one or more of:
a predetermined time schedule;
a rapid eye movement sleep state being detected;
a deep sleep state being detected;
a light sleep state being detected;
body movement;
breathing sounds and/or presence of snoring; or
breathing pattern.

10. A method, comprising:
outputting a composite signal, wherein the composite signal comprises:
a pilot tone of an ultrasonic reference frequency; and two auxiliary tones of equal amplitude;
wherein a first auxiliary tone of the two auxiliary tones has a first ultrasonic frequency that is offset below the ultrasonic reference frequency, the offset corresponding to a stimulus frequency, a second auxiliary tone has a second ultrasonic frequency that is offset above the ultrasonic reference frequency by the stimulus frequency, and each of the two auxiliary tones has an amplitude that is less than or equal to half the amplitude of the pilot tone, such that an envelope of the composite signal is a sinusoid at the stimulus frequency, and has a symmetrical spectral energy distribution about the ultrasonic reference frequency,
the method comprising sampling the composite signal reflected by a user and estimating motion of the user by determining a shift in a spectral energy distribution of the sampled reflected composite signal, relative to the ultrasonic reference frequency;
wherein the pilot tone and the two auxiliary tones combine to produce sinusoidal fluctuations in acoustic pressure at the stimulus frequency, wherein the pilot tone and the two auxiliary tones have frequencies in a range of 16 kHz to 48 KHz.

11. The method according to claim 10, further comprising modulating the two auxiliary tones according to a duty cycle in which stimulation is periodically reduced or removed.

12. A non-transitory computer readable medium having computer-readable instructions stored thereon, which, when executed by a processor, cause the processor to:
control a speaker to output a composite signal, wherein the composite signal comprises:
a pilot tone of the ultrasonic reference frequency; and two auxiliary tones of equal amplitude;
wherein a first auxiliary tone of the two auxiliary tones has a first ultrasonic frequency that is offset below the ultrasonic reference frequency, the offset corresponding to a stimulus frequency, a second auxiliary tone of the two auxiliary tones has a second ultrasonic frequency that is offset above the ultrasonic reference frequency by the stimulus frequency, and each of the first and second auxiliary tones has an amplitude that is less than or equal to half the amplitude of the pilot tone, such that an envelope of the composite signal is a sinusoid at the stimulus frequency, and has a symmetrical spectral energy distribution about the ultrasonic reference frequency;
control a microphone to receive the composite signal reflected by a user;
control a controller to sample the composite signal received by a microphone; and
control the controller to estimate motion of a user by determining a shift in a spectral energy distribution of the sampled reflected composite signal, relative to an ultrasonic reference frequency;
wherein the pilot tone and the two auxiliary tones combine to produce sinusoidal fluctuations in acoustic pressure at the stimulus frequency; and
wherein the pilot tone and the two auxiliary tones have frequencies in a range of 16 kHz to 48 KHz.

* * * * *